United States Patent [19]
Kondo et al.

[11] Patent Number: 5,972,607
[45] Date of Patent: *Oct. 26, 1999

[54] METHODS FOR NUCLEIC ACID AMPLIFICATION WITH THERMOSTABLE RIBONUCLEASE H

[75] Inventors: Motohiro Kondo; Toshiya Aono; Katsuya Daimon, all of Otu, Japan

[73] Assignee: Toyo Boseki Kabushiki Kaisha, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/893,023

[22] Filed: Jul. 15, 1997

[30] Foreign Application Priority Data

Jul. 16, 1996 [JP] Japan .................................. 8-185918

[51] Int. Cl.$^6$ .............................. C12Q 1/68; C12P 19/34; C12N 9/00; C07H 21/02
[52] U.S. Cl. ......................... 435/6; 435/91.2; 435/91.21; 435/91.51; 435/183; 536/23.1; 536/24.3; 536/24.31
[58] Field of Search ................................ 435/91.21, 91.2, 435/6, 91.51, 183; 536/23.1, 24.31, 24.3, 24.33, 25.3

[56] References Cited

U.S. PATENT DOCUMENTS

| 5,409,818 | 4/1995 | Davey et al. | 435/91.21 |
| 5,480,784 | 1/1996 | Kacian et al. | 435/91.21 |

FOREIGN PATENT DOCUMENTS

| 7-203999 | 8/1995 | Japan . | |
| WO 84/03285 | 8/1984 | WIPO . | |
| WO 88/10315 | 12/1988 | WIPO . | |
| WO 89/01050 | 2/1989 | WIPO . | |

OTHER PUBLICATIONS

Rapid and Simple Method for Purification of Nucleic Acids; Boom et al.; Journal of Clinical Microbiology Mar. 1990, p. 495–503, vol. 28, No. 3.

Preparation of Oligodeoxynucleotide–alkaline phosphatase conjugates and Their Use as Hybridization Probes Jablonski et al.; Nucleic Acids Research, vol. 14 No. 15, 1986, p. 6115–6128.

NASBA™ Isothermal Enzymatic In Vitro Nucleic Acid Amplification Optimized for the Diagnosis of HIV–Infection; Kievits et al.; Journal of Virological Methods, 35 (1991) p. 273–286.

*Primary Examiner*—Nancy Degen
*Assistant Examiner*—Andrew Wang
*Attorney, Agent, or Firm*—Leydig, Voit & Mayer, Ltd.

[57] ABSTRACT

Methods for nucleic acid amplification with thermostable ribonuclease H, in which single-stranded RNA (−) is prepared from RNA (+) as a target nucleic acid and the copy number of the single-stranded RNA (−) is increased through the use of thermostable ribonuclease H in combination with non-thermostable RNA-dependent DNA polymerase, non-thermostable DNA-dependent DNA polymerase and non-thermostable DNA-dependent RNA polymerase. In these methods, the number of amplification cycles is well increased and the sensitivity of detection can, therefore, be improved, as compared with the conventional methods. Also provided are methods for the detection of a target nucleic acid from RNA copies of a specific nucleic acid, obtained by any of the amplification methods, and reagent kits for use in these methods.

46 Claims, 5 Drawing Sheets

METHODS FOR NUCLEIC ACID AMPLIFICATION WITH THERMOSTABLE RIBONUCLEASE H

This application claims priority to Japanese patent application number 185918, filed Jul. 16, 1996.

FIELD OF INVENTION

The present invention relates to methods for nucleic acid amplification based on RNA replication. More particularly, it relates to methods for nucleic acid amplification with thermostable ribonuclease H, methods for the detection of a target nucleic acid from RNA copies of a specific nucleic acid, obtained by any of the amplification methods, and reagent kits for use in these methods.

BACKGROUND OF THE INVENTION

In recent years, there have been developed various methods for the diagnosis of diseases by detection of associated genes from bacteria, viruses or other pathogens. Some samples may contain nucleic acids in sufficient amounts for their direct detection. In contrast, when a target gene is present in a very small amount or proportion, the direct detection of the target gene becomes quite difficult. This problem has hitherto been solved with a technique of amplifying the target gene by cell or bacterial culture methods; however, these methods have a defect that they require much time.

For nucleic acid amplification, the polymerase chain reaction (PCR) method has also been known. In this method, the degree of amplification of a target nucleic acid is controlled by the number of cycles. The amplification rate is calculated by $2^n$ where n is the number of cycles. The amplification of a target nucleic acid up to the amount making possible its actual detection requires 25 to 30 cycles.

Different methods for nucleic acid amplification based on RNA replication are disclosed in JP-A 2-5864, JP-A 2-500565 and JP-A 2-501532. In these methods, a promoter sequence for DNA-dependent RNA polymerase is incorporated into a primer for use in the synthesis of double-stranded DNA from a target nucleic acid. After the synthesis of double-stranded DNA, the resulting double-stranded DNA is used as a template to synthesize RNA corresponding to the target nucleic acid with DNA-dependent RNA polymerase.

The resulting RNA is then used for the synthesis of a DNA/RNA hybrid with RNA-dependent DNA polymerase, from which DNA/RNA hybrid the RNA is separated to yield single-stranded DNA. The DNA separation is achieved by heat denaturation (JP-A 2-500565 and JP-A 2-501532) or by use of ribonuclease H (JP-A 2-5864).

The single-stranded DNA thus obtained is used together with another primer to synthesize double-stranded DNA containing a promoter sequence for DNA-dependent RNA polymerase, and the resulting double-stranded DNA is subjected to RNA transcription.

The use of this method makes it possible to transcribe tens or thousands of RNA molecules from only one double-stranded nucleic acid molecule by DNA-dependent RNA polymerase, resulting in a higher efficiency of amplification per cycle as compared with the PCR method. In the case where ribonuclease H is used, temperature cycles, required in the PCR method, become unnecessary, and amplification can, therefore, be carried out in a simpler manner.

The amplification methods based on RNA replication have high efficiency of amplification; however, the conventional enzymes used in the respective reactions, such as RNA-dependent DNA polymerase, DNA-dependent RNA polymerase and DNA-dependent DNA polymerase, are usually non-thermostable. Low thermostability of these enzymes prevents the use of high temperatures in the reactions of amplification; therefore, non-specific hybridization between the template nucleic acid and the primer cannot be avoided, resulting in a decrease of specificity, which may cause a deterioration in the sensitivity of detection. To solve this problem, there has been developed a method with thermostable enzymes derived from *Thermus thermophilus* as the enzymes to be used in these amplification methods (JP-A 7-203999). In this method, the reactions of amplification are effected at a constant high temperature by use of thermostable enzymes, thereby making it possible to avoid non-specific hybridization.

SUMMARY OF THE INVENTION

An object of the present invention is to provide methods for nucleic acid amplification based on RNA replication, in which the reactions of amplification are effected without replacing all enzymes by thermostable enzymes and without raising the reaction temperatures to improve the sensitivity of detection. The other objects of the present invention will be understood upon reading the following description.

Thus, the present invention provides a method for nucleic acid amplification with thermostable ribonuclease H, wherein single-stranded RNA (−) is prepared from RNA (+) and the copy number of the single-stranded RNA (−) is increased, comprising the use of non-thermostable RNA-dependent DNA polymerase, non-thermostable DNA-dependent DNA polymerase, non-thermostable DNA-dependent RNA polymerase and thermostable ribonuclease H. The term "ribonuclease" may herein be often referred to as "RNase."

The present invention further provides another method for nucleic acid amplification with thermostable ribonuclease H, wherein single-stranded RNA (−) is prepared from RNA (+) as a target nucleic acid and the copy number of the single-stranded RNA (−) is increased, comprising the steps of:

(1) optionally extracting RNA (+) as a target nucleic acid from a sample;

(2) hybridizing a first primer to the RNA (+) in step (1) as a template, the first primer having a sequence complementary to the RNA (+) sequence and a promoter sequence for non-thermostable DNA-dependent RNA polymerase on the 5'-end thereof; and effecting a reaction of DNA extension with non-thermostable RNA-dependent DNA polymerase to yield an RNA/DNA hybrid extension product;

(3) cleaving the RNA from the RNA/DNA hybrid extension product in step (2) with thermostable ribonuclease H capable of specifically cleaving only RNA from any RNA/DNA hybrid, to yield single-stranded DNA;

(4) hybridizing a second primer to the single-stranded DNA in step (3) as a template, the second primer having a sequence complementary to the single-stranded DNA sequence; and effecting a reaction of DNA extension with non-thermostable DNA-dependent DNA polymerase to yield a double-stranded DNA intermediate having a functionable promoter sequence upstream from the 5'-end thereof;

wherein the nucleic acid sequence of the first primer is sufficiently complementary to the target nucleic acid, RNA (+) sequence, and the nucleic acid sequence of the second primer is sufficiently homologous to the target nucleic acid, RNA (+) sequence, and the 3'-end of the first primer is directed to the 3'-end of the second primer on the complementary strand;

(5) increasing the copy number of single-stranded RNA (−) from the double-stranded DNA intermediate in step (4) with non-thermostable DNA-dependent RNA polymerase capable of recognizing the promoter sequence therefor;

(6) hybridizing the second primer to the single-stranded RNA (−) in step (5) as a template, the second primer having a sequence complementary to the single-stranded RNA (−) sequence, which second primer is the same as that used in step (4) and having a sequence sufficiently homologous to the RNA (+) sequence; and effecting a reaction of DNA extension with non-thermostable RNA-dependent DNA polymerase to yield an RNA/DNA hybrid extension product;

(7) cleaving the RNA from the RNA/DNA hybrid extension product in step (6) with thermostable ribonuclease H capable of specifically cleaving only RNA from any RNA/DNA hybrid, to yield single-stranded DNA;

(8) hybridizing the first primer to the single-stranded DNA in step (7) as a template, the first primer having a sequence complementary to the single-stranded DNA and a promoter sequence for non-thermostable DNA-dependent RNA polymerase on the 5'-end thereof, which first primer is the same as that used in step (2) and having a sequence sufficiently complementary to the RNA (+) sequence; and effecting a reaction of DNA extension with non-thermostable DNA-dependent DNA polymerase to yield a double-stranded DNA intermediate having a functionable promoter sequence upstream from the 5'-end thereof;

(9) increasing the copy number of single-stranded RNA (−) from the double-stranded DNA intermediate in step (8) with non-thermostable DNA-dependent RNA polymerase capable of recognizing the promoter sequence therefor; and

(10) optionally repeating steps (6) to (9) with the resulting single-stranded RNA (−) as a template.

The present invention further provides another method for nucleic acid amplification with thermostable ribonuclease H, wherein single-stranded RNAs (+) and (−) are prepared from RNA (+) as a target nucleic acid and the copy numbers of the single-stranded RNAs (+) and (−) are increased, comprising the steps of:

(1) optionally extracting RNA (+) as a target nucleic acid from a sample;

(2) hybridizing a first primer to the RNA (+) in step (1) as a template, the first primer having a sequence complementary to the RNA (+) sequence and a promoter sequence for non-thermostable DNA-dependent RNA polymerase on the 5'-end thereof; and effecting a reaction of DNA extension with non-thermostable RNA-dependent DNA polymerase to yield an RNA/DNA hybrid extension product;

(3) cleaving the RNA from the RNA/DNA hybrid extension product in step (2) with thermostable ribonuclease H capable of specifically cleaving only RNA from any RNA/DNA hybrid, to yield single-stranded DNA;

(4) hybridizing a second primer to the single-stranded DNA in step (3) as a template, the second primer having a sequence complementary to the single-stranded DNA sequence and a promoter sequence for non-thermostable DNA-dependent RNA polymerase on the 5'-end thereof; and effecting a reaction of DNA extension with non-thermostable DNA-dependent DNA polymerase to yield a double-stranded DNA intermediate having functionable promoter sequences upstream from the 5'-end thereof;

wherein the nucleic acid sequence of the first primer is sufficiently complementary to the target nucleic acid, RNA (+) sequence, the nucleic acid sequence of the second primer is sufficiently homologous to the target nucleic acid, RNA (+) sequence, and the 3'-end of the first primer is directed to the 3'-end of the second primer on the complementary strand;

(5) increasing the copy numbers of single-stranded RNAs (+) and (−) from the double-stranded DNA intermediate in step (4) with non-thermostable DNA-dependent RNA polymerase capable of recognizing the promoter sequence therefor;

(6) hybridizing the first and second primers, which are the same as used in steps (2) and (4), respectively, to the single-stranded RNAs (+) and (−) in step (5), respectively, as templates; and effecting reactions of DNA extension with non-thermostable RNA-dependent DNA polymerase to yield RNA/DNA hybrid extension products;

(7) cleaving the RNA from the RNA/DNA hybrid extension products in step (6) with thermostable ribonuclease H capable of specifically cleaving only RNA from any RNA/DNA hybrid, to yield single-stranded DNAs (+) and (−);

(8) hybridizing the first and second primers, which are the same as used in steps (2) and (4), respectively, to the single-stranded DNAs (+) and (−) in step (7), respectively, as a template; and effecting reactions of DNA extension with non-thermostable DNA-dependent DNA polymerase to yield a double-stranded DNA intermediate having functionable promoter sequences upstream from the 5'-end thereof;

(9) increasing the copy numbers of single-stranded RNAs (+) and (−) from the double-stranded DNA intermediate in step (8) with non-thermostable DNA-dependent RNA polymerase capable of recognizing the promoter sequence therefor; and

(10) optionally repeating steps (6) to (9) with the resulting single-stranded RNAs (+) and (−) as templates.

The present invention further provides another method for nucleic acid amplification with thermostable ribonuclease H, wherein single-stranded RNA (−) is prepared from DNA (+) as a target nucleic acid sequence and the copy number of the single-stranded RNA (−) is increased, comprising the steps of:

(1) optionally extracting DNA (+) as a target nucleic acid sequence from a sample;

(2) hybridizing a first primer to the DNA (+) in step (1), the first primer having a sequence complementary to the DNA (+) sequence and a promoter sequence for non-thermostable DNA-dependent RNA polymerase on the 5'-end thereof; and effecting a reaction of DNA extension with non-thermostable DNA-dependent DNA polymerase to yield a double-stranded DNA;

(3) separating single-stranded DNA from the double-stranded DNA in step (2) by denaturation;

(4) hybridizing a second primer to the single-stranded DNA in step (3), the second primer having a sequence homologous to the DNA (+) sequence; and effecting a reaction of DNA extension with non-thermostable DNA-dependent DNA polymerase to yield a double-stranded DNA intermediate having a functionable promoter sequence upstream from the 5'-end thereof;

(5) synthesizing a plurality of single-stranded RNAs (−) from the double-stranded DNA intermediate in step (4) with non-thermostable DNA-dependent RNA polymerase;

(6) hybridizing a second primer to the single-stranded RNA (−) in step (5) as a template, the second primer having a sequence complementary to the single-stranded RNA (−) sequence, which second primer is the same as that used in step (4) and having a sequence sufficiently homologous to the DNA (+) sequence; and effecting a reaction of DNA extension with non-thermostable RNA-dependent DNA polymerase to yield an RNA/DNA hybrid extension product;

(7) cleaving the RNA from the RNA/DNA hybrid extension product in step (6) with thermostable ribonuclease H capable of specifically cleaving only RNA from any RNA/DNA hybrid, to yield single-stranded DNA;

(8) hybridizing a first primer to the single-stranded DNA in step (7) as a template, the first primer having a sequence complementary to the single-stranded DNA sequence and a promoter sequence for non-thermostable DNA-dependent RNA polymerase on the 5'-end thereof, which first primer is the same as that used in step (2) and having a sequence sufficiently complementary to the DNA (+) sequence; and effecting a reaction of DNA extension with non-thermostable DNA-dependent DNA polymerase to yield a double-stranded DNA intermediate having a functionable promoter sequence upstream from the 5'-end thereof;

(9) increasing the copy number of single-stranded RNA (−) from the double-stranded DNA intermediate in step (8) with non-thermostable DNA-dependent RNA polymerase capable of recognizing the promoter sequence therefor; and

(10) optionally repeating steps (6) to (9) with the resulting single-stranded RNA (−) as a template.

The present invention further provides another method for nucleic acid amplification with thermostable ribonuclease H, wherein single-stranded RNAs (+) and (−) are prepared from DNA (+) as a target nucleic acid and the copy number of the single-stranded RNAs (+) and (−) is increased, comprising the steps of:

(1) optionally extracting DNA (+) as a target nucleic acid from a sample;

(2) hybridizing a first primer to the DNA (+) in step (1), the first primer having a sequence complementary to the DNA (+) sequence and a promoter sequence for non-thermostable DNA-dependent RNA polymerase on the 5'-end thereof; and effecting a reaction of DNA extension with non-thermostable DNA-dependent DNA polymerase to yield a double-stranded DNA;

(3) separating single-stranded DNA from the double-stranded DNA in step (2) by denaturation;

(4) hybridizing a second primer to the single-stranded DNA in step (3), the second primer having a sequence homologous to the DNA (+) sequence and a promoter sequence for non-thermostable DNA-dependent RNA polymerase on the 5'-end thereof; and effecting a reaction of DNA extension with non-thermostable DNA-dependent DNA polymerase to yield a double-stranded DNA intermediate having functionable promoter sequences upstream from the 5'-end thereof;

(5) synthesizing a plurality of single-stranded RNAs (+) and (−) from the double-stranded DNA intermediate in step (4) with non-thermostable DNA-dependent RNA polymerase;

(6) hybridizing the first and second primers, which are the same as used in steps (2) and (4), respectively, to the single-stranded RNAs (+) and (−) in step (5), respectively, as templates; and effecting reactions of DNA extension with non-thermostable RNA-dependent DNA polymerase to yield RNA/DNA hybrid extension products;

(7) cleaving the RNA from the RNA/DNA hybrid extension products in step (6) with thermostable ribonuclease H capable of specifically cleaving only RNA from any RNA/DNA hybrid, to yield single-stranded DNAs (+) and (−);

(8) hybridizing the first and second primers, which are the same as used in steps (2) and (4), respectively, to the single-stranded DNAs (+) and (−) in step (7), respectively, as templates; and effecting reactions of DNA extension with non-thermostable DNA-dependent DNA polymerase to yield a double-stranded DNA intermediate having functionable promoter sequences upstream from the 5'-end thereof;

(9) increasing the copy numbers of single-stranded RNAs (+) and (−) from the double-stranded DNA intermediate in step (8) with non-thermostable DNA-dependent RNA polymerase capable of recognizing the promoter sequence therefor; and

(10) optionally repeating steps (6) to (9) with the resulting single-stranded RNAs (+) and (−) as templates.

The present invention further provides a method for the detection of a target nucleic acid in a sample, comprising amplifying a target nucleic acid in a sample by any of the above methods for nucleic acid amplification; hybridizing the amplified nucleic acid to a detection probe; and detecting the hybridized nucleic acid.

The present invention further provides a reagent kit for use in the amplification of a specific nucleic acid, comprising the reagents:

(a) a first primer having a sequence complementary to the sequence of RNA (+) as the nucleic acid and a promoter sequence for non-thermostable DNA-dependent RNA polymerase on the 5'-end thereof;

(b) a second primer having a sequence homologous to the RNA (+) sequence;

(c) thermostable ribonuclease H;

(d) non-thermostable DNA-dependent RNA polymerase;

(e) non-thermostable RNA-dependent DNA polymerase;

(f) non-thermostable DNA-dependent DNA polymerase;

(g) ribonucleoside triphosphates;

(h) deoxyribonucleoside triphosphates; and (i) a buffer.

The present invention further provides another reagent kit for use in the amplification of a specific nucleic acid sequence, comprising the reagents:

(a) a first primer having a sequence complementary to the sequence of RNA (+) as the nucleic acid and a promoter sequence for non-thermostable DNA-dependent RNA polymerase on the 5'-end thereof;

(b) a second primer having a sequence homologous to the RNA (+) sequence and a promoter sequence for non-thermostable DNA-dependent RNA polymerase on the 5'-end thereof;

(c) thermostable ribonuclease H;
(d) non-thermostable DNA-dependent RNA polymerase;
(e) non-thermostable RNA-dependent DNA polymerase;
(f) non-thermostable DNA-dependent DNA polymerase;
(g) ribonucleoside triphosphates;
(h) deoxyribonucleoside triphosphates; and
(i) a buffer.

DETAILED DESCRIPTION OF THE INVENTION

Figure 1:
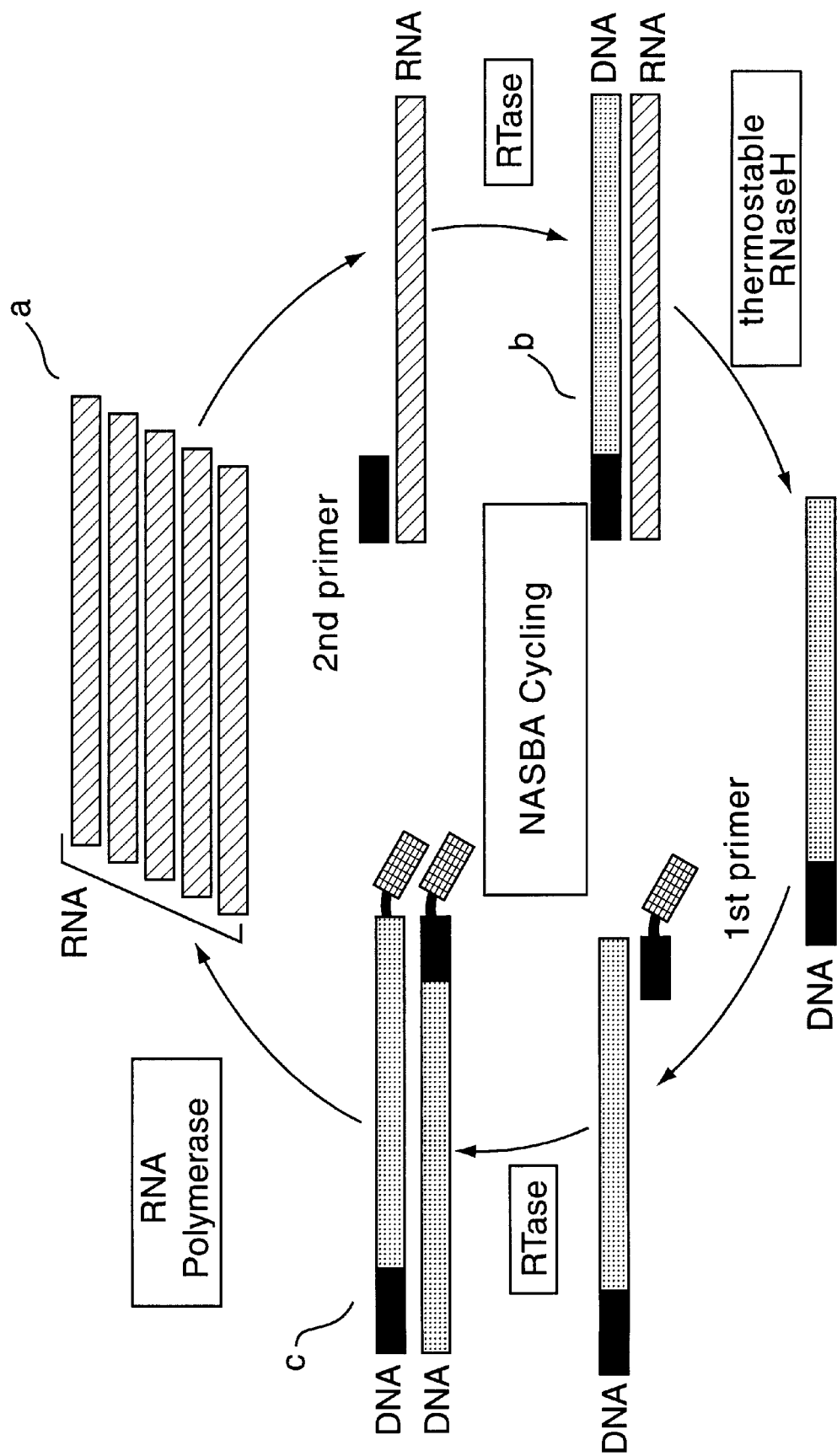
FIG. 1 is a schematic diagram showing the amplification cycle of single-stranded RNA when only the first primer has a promoter sequence.

In the methods of the present invention, the target nucleic acid may be either DNA or RNA. When the target nucleic acid is in the double-stranded form, or when the target nucleic acid has higher-order structure, even in the single-stranded form, it may be previously converted into the simple single-stranded form by denaturation with heating, acids, alkalis or any other treatment, and then subjected to the reactions of amplification.

When the target nucleic acid is present in a mixture of proteins, lipids or carbohydrates, or in a biological sample, it may optionally be extracted according to the ordinary method, and then utilized in the methods for nucleic acid amplification or detection of the present invention. In a specific means of extraction, a sample is incubated with the addition of a solution containing a proteinase or surfactant for about 30 minutes, and the resulting solution is then extracted with, for example, phenol or chloroform, followed by ethanol precipitation, to yield a nucleic acid. Alternatively, chaotropic agents and carriers of silica particles may be used.

The terms "RNA (+)" and "RNA (-)" used herein refer to a couple of RNAs one having a sequence complementary to the other. These terms further mean that RNA (+) or (-) has a sequence homologous to the corresponding DNA (+) or (-) sequence, respectively.

The term "reactions of extension" used herein refers to a chain of reactions to synthesize DNA having a sequence complementary to the target nucleic acid sequence, in which a primer having a sequence sufficiently complementary to the nucleic acid sequence is hybridized to the nucleic acid as a template and deoxynucleotides are covalently bound to the primer, successively, in the presence of DNA-dependent DNA polymerase, deoxyadenosine 5'-triphosphate (dATP), deoxycytidine 5'-triphosphate (dCTP), deoxyguanosine 5'-triphosphate (dGTP) and deoxythymidine 5'-triphosphate (dTTP).

The term "promoter sequence" used herein refers to a sequence to which non-thermostable DNA-dependent RNA polymerase specifically binds and acts, examples of which are those for T7 RNA polymerase. The non-thermostable DNA-dependent RNA polymerase specifically binds to the promoter sequence and synthesizes an RNA having a sequence homologous to the DNA sequence downstream from the promoter sequence.

The term "thermostable ribonuclease (RNase) H" used herein refers to any RNase H having excellent thermostability as compared with RNase H derived from *Escherichia coli*. Examples of such an enzyme include RNase H isolated and purified from thermostable bacteria, and RNase H derived from *E. coli* and modified so as to have thermostability. Some of these enzymes may usually have the residual activity of 50% or more, even if treated at 50° to 90° C. for 10 minutes. For the methods of the present invention, RNase H isolated from thermostable bacteria and purified is preferred with Tth RNase H derived from *Thermus thermophilus* being more preferred.

The most preferred concentration of thermostable RNase H is obtained by the addition of 0.001 to 0.1 U of the enzyme to 20 μl of the reaction system. When it is higher than 0.1 U, single-stranded RNA may be cleaved in a moment of primer binding, resulting in no reactions of amplification. When it is lower than 0.001 U, the separation of the first primer extension product from the single-stranded RNA is difficult to occur, causing a deterioration in the sensitivity of detection. Thus, for the purpose of attaining high sensitivity, thermostable RNase H may be used within the range of concentrations as described above.

The term "non-thermostable enzyme" used herein refers to any enzyme having an optimum temperature around the ordinary temperature. For example, non-thermostable RNA-dependent DNA polymerase is an enzyme capable of synthesizing DNA from an oligodeoxyribonucleotide primer and an RNA template, and this enzyme may further have DNA-dependent DNA polymerase activity. Examples of this enzyme include avian myoblastoma virus polymerase (AMV reverse transcriptase) and Maloney mouse leukemia virus polymerase (MMLV reverse transcriptase). Any other RNA-dependent DNA polymerase derived from eucaryotic cells may be used.

Non-thermostable DNA-dependent RNA polymerase is an enzyme capable of binding to a promoter sequence and specifically initiating the in vitro synthesis of RNA at the prescribed initiation site in close proximity to the promoter sequence. Examples of this enzyme include bacteriophage T7 RNA polymerase, T3 RNA polymerase, SP6 RNA polymerase, phage φII polymerase, Salmonella phage sp6 polymerase and Pseudomonas phage gh-1 polymerase. Particularly preferred are T7 RNA polymerase, T3 RNA polymerase and SP6 RNA polymerase.

Non-thermostable DNA-dependent DNA polymerase is an enzyme capable of synthesizing DNA from an oligodeoxyribonucleotide primer and a DNA template. Many DNA polymerases may be used, for example, DNA polymerases derived from eucaryotic cells, including polymerase α or β; DNA polymerases isolated from mammalian tissues such as calf thymi; Klenow fragments of *E. coli* polymerase I; and bacteriophage T7 DNA polymerase. Preferred are enzymes such as AMV reverse transcriptase.

Particularly preferred is the use of an enzyme having both RNA-dependent DNA polymerase activity and DNA-dependent DNA polymerase activity.

The first primer used in the present invention has a nucleic acid sequence sufficiently complementary to the target nucleic acid sequence, RNA or DNA, and further have a promoter sequence as described above, on the 5'-end side thereof. The 3'-end of the first primer is directed to the 3'-end of another primer on the complementary strand.

The promoter sequence used in the present invention is not particularly limited. For example, in the case of T7 RNA polymerase, the following promoter sequence is known:

5'-AAT TCT AAT ACG ACT CAC TAT AGG G-3' (SEQ ID NO: 1)

Other examples of the promoter sequence include:

5'-ATT AAC CCT CAC TAA AG-3' (SEQ ID NO: 2) for T3 RNA polymerase, and

5'-ATT TAG GTG ACA CTA TA-3' (SEQ ID NO: 3) for SP6 RNA polymerase.

The promoter sequence used together with non-thermostable DNA-dependent RNA polymerase in the present invention is preferably selected from, but not limited to, the above three sequences. Particularly preferred is the use of T7 RNA polymerase and the corresponding promoter sequence.

In general, a promoter sequence may have a spacer following to the initiation point of replication. In necessary, an arbitrary sequence may be combined to the 3'-end of the promoter sequence. Depending upon the amplification region, the efficiency of amplification can be improved by the insertion of a spacer sequence.

The second primer used in the present invention has a nucleic acid sequence complementary to the nucleic acid sequence of the first primer extension product and sufficiently homologous to the target nucleic acid sequence, RNA or DNA. If necessary, the second primer may further have a promoter sequence on the 5'-end side thereof. The 3'-end of the second primer is directed to the 3'-end of another primer on the complementary strand.

When the second primer has a promoter sequence, the promoter sequence may be the same as or different from that of the first primer. If they are different, a plurality of non-thermostable DNA-dependent RNA polymerases are used which act on the respective promoter sequences. For example, T7 RNA polymerase is used, when T7 promoter is used as the promoter sequence of the second primer; T3 RNA polymerase when T3 promoter is used; and SP6 RNA polymerase when SP6 promoter is used. The non-thermostable DNA-dependent RNA polymerase and the corresponding promoter sequence are preferably selected from, but not limited to, the above three combinations. Particularly preferred is the use of T7 RNA polymerase and the corresponding promoter sequence.

When the second primer has a promoter sequence, the promoter sequence for T7 RNA polymerase is preferably used for the first and second primers to amplify the copy number by use of T7 RNA polymerase.

The length of a region of the first or second primer to be hybridized to the target nucleic acid sequence is not particularly limited. Preferred is 10 to 100 bp, more preferably 10 to 50 bp, and particularly preferably 18 to 30 bp, but not limited thereto.

The oligonucleotides used as the first and second primers can be synthesized by the phosphoamidite method using, for example, DNA synthesizer model 391 (Parkin Elmer). The deprotection of each oligonucleotide is achieved with ammonia water. The purification may be carried out by FPLC on a reverse phase column. Other synthesis methods may include the phosphoric triester method, H-phosphonate method and thiophosphite method. Alternatively, the oligonucleotides may be isolated from various biological sources such as restriction endonuclease digests.

The reaction conditions used in the present invention may be those which ensure the rapid proceeding of the above enzyme reactions. More particularly, the reactions are effected in buffers suitable for the respective reactions at a temperature of about 37° to about 45° C. In the methods of the present invention, higher reactivity can be attained characteristically by the reaction of thermostable RNase H at temperatures ranging from about 37° to about 45° C., as compared with the case where the conventional non-thermostable RNase H is used. The amplification cycle in the methods of the present invention is continued till these enzymes become deactivated; however, the substitution of a thermostable enzyme only for RNase H results in that the number of amplification cycles is well increased and the sensitivity of detection can, therefore, be improved.

The present invention will be explained by reference to the drawings.

The methods of the present invention are based on the amplification cycle shown in FIG. 1.

STEP (1)

Using single-stranded RNA (−, a) as a template, a second primer having a sequence complementary to the single-stranded RNA (−) sequence (and homologous to the corresponding RNA (+) sequence) is hybridized to the 3'-region of the single-stranded RNA (−), and the reaction of DNA extension is effected with non-thermostable RNA-dependent DNA polymerase to synthesize a second primer extension product (+, b), resulting in an RNA/DNA hybrid extension product. The non-thermostable RNA-dependent DNA polymerase used in this step is preferably AMV reverse transcriptase.

STEP (2)

To separate the single-stranded DNA (+, b) from the RNA/DNA hybrid extension product in step (1), only the single-stranded RNA (−, a) binding to the second primer extension product (+, b) is specifically cleaved with thermostable ribonuclease (RNase) H. The thermostable RNase H has the property of cleaving only RNA binding to DNA, so that only the single-stranded RNA (−, a) is cleaved.

STEP (3)

Using the second primer extension product (+, b) separated in step (2) as a template, a first primer having a sequence complementary to the single-stranded DNA (+) (i.e., a sequence homologous to the single-stranded RNA (−) sequence and complementary to the corresponding RNA (+) sequence) and a promoter sequence for non-thermostable DNA-dependent RNA polymerase on the 5'-end thereof is hybridized to the 3'-region of the single-stranded DNA (+), and a first primer extension product is synthesized with non-thermostable DNA-dependent DNA polymerase, resulting in a double-stranded DNA intermediate (c) having a functionable promoter sequence upstream from the 5'-end thereof. In this step, DNA-dependent DNA polymerase activity possessed by AMV reverse transcriptase may be utilized, and there is no need for the addition of DNA-dependent DNA polymerase as a separate enzyme.

STEP (4)

From the double-stranded DNA intermediate obtained in step (3) and having a functionable promoter sequence bound to the upstream region thereof, the copy number of the single-stranded RNA (−, a) is increased with non-thermostable DNA-dependent RNA polymerase capable of recognizing the promoter sequence therefor.

The non-thermostable DNA-dependent RNA polymerase can synthesize 50 to 1000 copies of the single-stranded RNA (−, a) from one template. Therefore, when this cycle is repeated at least 5 times, at least hundred millions of copies of the amplification product RNA (−, a) can be obtained from one copy of the single-stranded RNA (−, a).

For the amplification of a nucleic acid from a biological sample based on the amplification cycle shown in FIG. 1, it is necessary to obtain a single-stranded RNA among from the nucleic acids in the sample. The knowledge of the degree of amplification of the single-stranded RNA obtained from the biological sample reveals the presence and concentration of a target nucleic acid in the sample.

Figure 2:
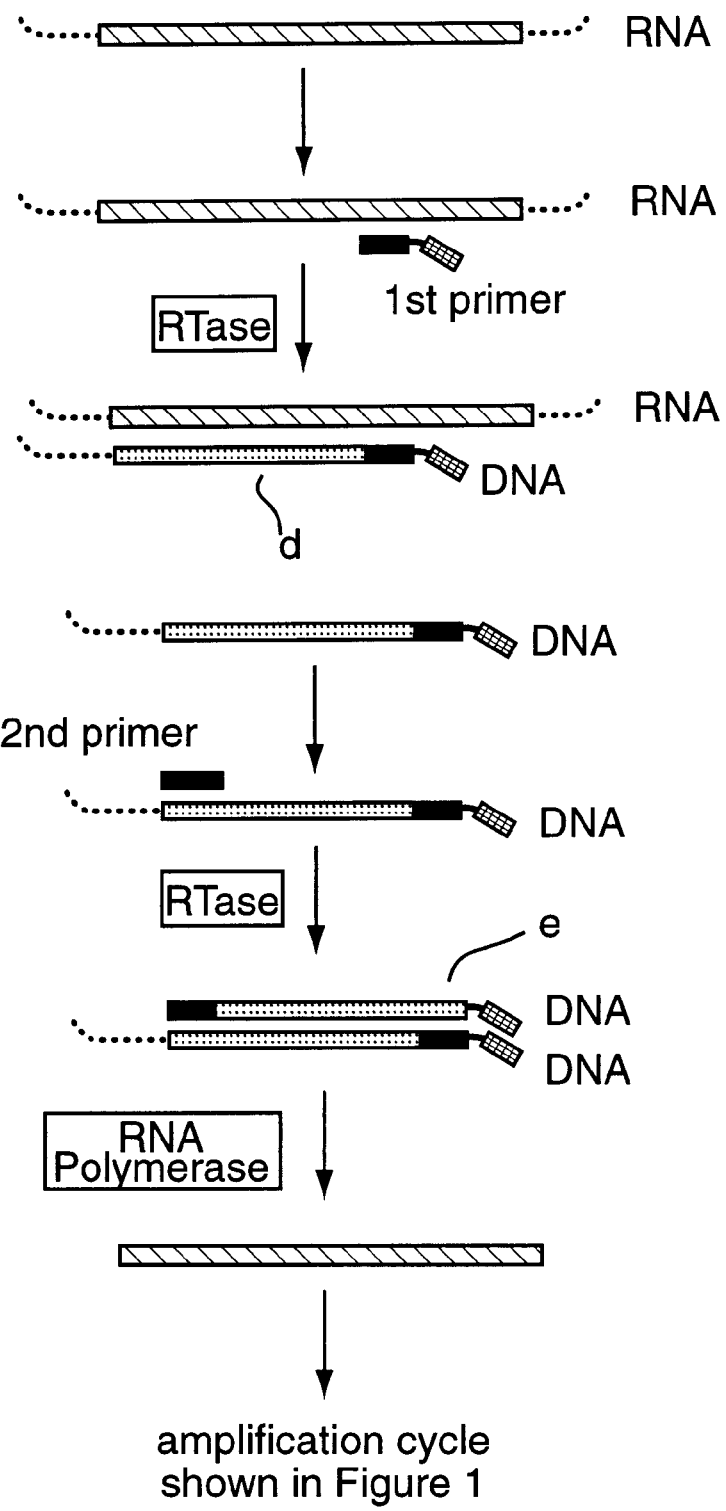
FIG. 2 is a schematic diagram showing a method for amplification of single-stranded RNA when the target nucleic acid is RNA.
Figure 3:
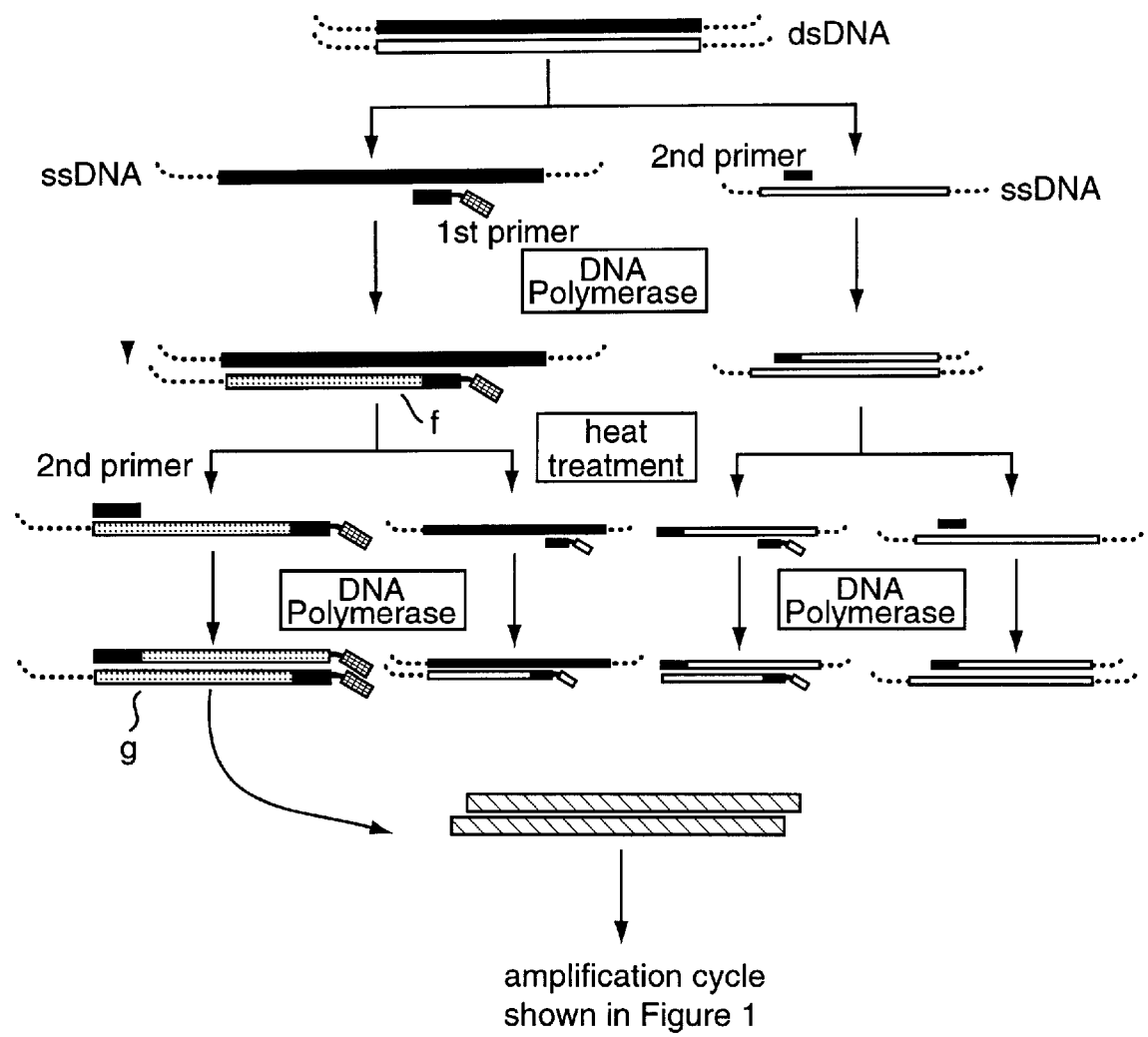
FIG. 3 is a schematic diagram showing a method for amplification of single-stranded DNA when the target nucleic acid is DNA.

FIG. 2 shows the amplification method in which a target nucleic acid is RNA, and FIG. 3 shows the amplification method in which a target nucleic acid is DNA. The preparation of a nucleic acid from the sample may be achieved by the pretreatment method as described above.

The following will describe the case where a target nucleic acid is RNA (+) as shown in FIG. 2.

STEP (1)

Using RNA (+) as a template, a first primer having a sequence complementary to the RNA (+) sequence and a promoter sequence for non-thermostable DNA-dependent RNA polymerase on the 5'-end thereof is hybridized to the template. In some cases hybridization may be effected only by the addition of a primer; however, to increase the efficiency of hybridization, the mixture may be treated at 65° C. for about 5 minutes. Although the mixture may be treated at 95° C., there is a possibility that the RNA may be cleaved. The non-thermostable DNA-dependent RNA polymerase and promoter sequence used in this step are the same enzyme and base sequence as used in the amplification cycle shown in FIG. 1. Then, a reaction of DNA extension from the first primer is effected with non-thermostable RNA-dependent DNA polymerase to synthesize a first primer extension product (−, d) having a sequence complementary to the target nucleic acid, RNA (+) sequence, resulting in an RNA/DNA hybrid extension product.

STEP (2)

To separate the first primer extension product (−, d) from the RNA/DNA hybrid extension product in step (1), the target nucleic acid, RNA (+) sequence is digested with thermostable RNase H, resulting in the single-stranded DNA (−, d).

STEP (3)

Using the single-stranded DNA (−, d) in step (2) as a template, a second primer having a sequence complementary to the single-stranded DNA (−, d) (i.e., a sequence homologous to the RNA (+) sequence) is hybridized to the 3'-region of the first primer extension product (−, d), and a reaction of DNA extension is effected with non-thermostable DNA-dependent DNA polymerase, resulting in a double-stranded DNA intermediate (e) having a functionable promoter sequence upstream from the 5'-end thereof.

The nucleic acid sequence of the first primer is sufficiently complementary to the target nucleic acid, RNA (+) sequence, and the nucleic acid sequence of the second primer is sufficiently homologous to the target nucleic acid, RNA (+) sequence, and the 3'-end of the first primer is directed to the 3'-end of the second primer on the complementary strand.

STEP (4)

From the double-stranded DNA intermediate (e) obtained in step (3), a plurality of single-stranded RNAs (−) are synthesized with non-thermostable DNA-dependent RNA polymerase capable of recognizing the promoter sequence therefor, and then subjected to the amplification cycle shown in FIG. 1, thereby increasing the copy number of the single-stranded RNA (−).

If necessary, the presence of a target nucleic acid sequence in a sample can be known by detection of the amplified single-stranded RNA (−) with a probe.

The following will describe the case where a target nucleic acid is DNA (+) as shown in FIG. 3, left end.

STEP (1)

When a target nucleic acid is double-stranded DNA, it is converted into single-stranded DNA (+).

STEP (2)

To the single-stranded DNA (+) in step (1), a first primer having a sequence complementary to the single-stranded DNA (+) and a promoter sequence for non-thermostable DNA-dependent RNA polymerase on the 5'-end thereof is hybridized. In some cases hybridization may be effected only by the addition of a primer; however, to increase the efficiency of hybridization, the mixture may be treated at 95° C. for about 5 minutes. The non-thermostable DNA-dependent RNA polymerase and promoter sequence used in this step are the same enzyme and base sequence as used in the amplification cycle shown in FIG. 1. Then, a reaction of DNA extension from the first primer is effected with non-thermostable RNA-dependent DNA polymerase to synthesize a first primer extension product (−) having a sequence complementary to the single-stranded DNA (+) sequence, resulting in double-stranded DNA (f).

STEP (3)

To separate the first primer extension product DNA (−) from the double-stranded DNA (f) in step (2), denaturation is carried out, which may be achieved by heat, acid, alkali or any other treatment. The heat treatment can be carried out in a simple manner.

STEP (4)

To the single-stranded DNA (−) separated in step (4), a second primer having a sequence homologous to the corresponding DNA (+) is hybridized, and a reaction of DNA extension is effected with non-thermostable DNA-dependent DNA polymerase to produce a double-stranded DNA intermediate (g) having a functionable promoter sequence bound to the upstream region thereof.

STEP (5)

Then, from the resulting double-stranded DNA intermediate (g) in step (4), a plurality of single-stranded RNAs (−) are synthesized with non-thermostable DNA-dependent RNA polymerase.

STEP (6)

The single-stranded RNA (−) obtained in step (5) is used as a template and subjected to the amplification cycle shown in FIG. 1, thereby increasing the copy number of single-stranded RNA (−).

If necessary, the presence of a target nucleic acid in a sample can be known by detection of the amplified single-stranded RNA (−) with a probe.

In FIGS. 1 to 3, the cases have been explained where only the first primer has a promoter sequence for non-thermostable DNA-dependent RNA polymerase. The following will describe a method for increasing the copy numbers of single-stranded RNA (−) and RNA (+) complementary thereto, in which both the first and second primers have promoter sequences for non-thermostable DNA-dependent RNA polymerase.

Figure 4:
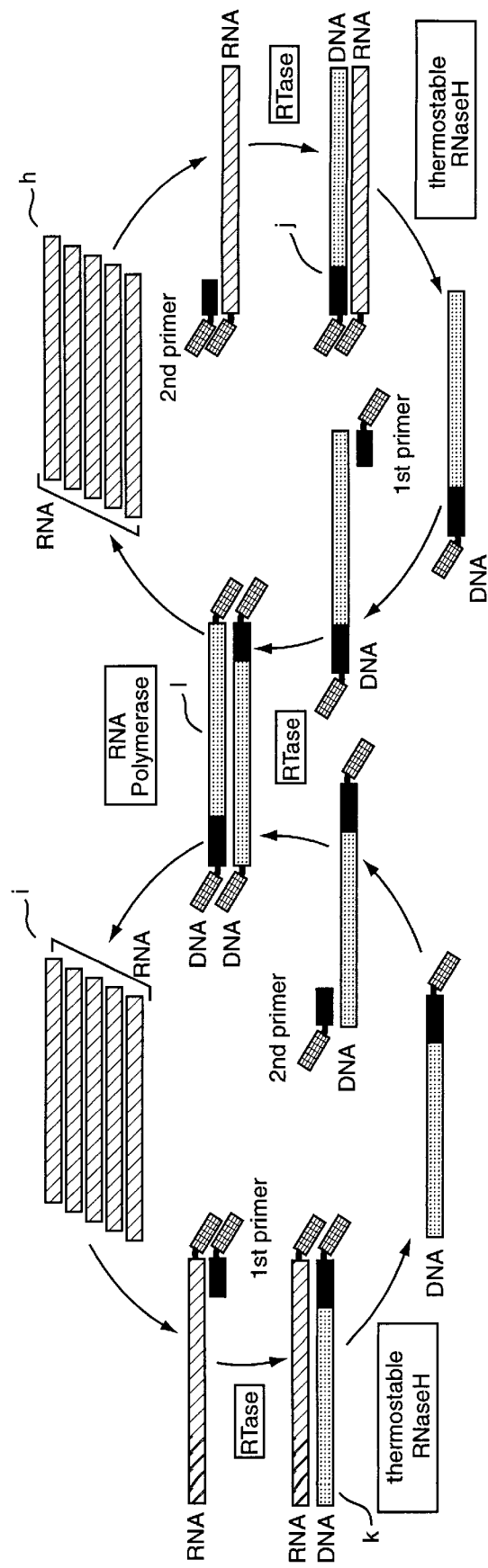
FIG. 4 is a schematic diagram showing the amplification cycle of single-stranded RNA when the first and second primers have promoter sequences.

In this method, as shown in FIG. 4, single-stranded RNA (−) and RNA (+) complementary thereto are amplified through the common double-stranded DNA intermediate (1) having functionable promoter sequences bound to both upstream and down-stream regions thereof.

Basically, the reaction mechanism in this method is substantially the same as described above, except that a promoter sequence for non-thermostable DNA-dependent RNA polymerase is bound to the second primer.

The promoter sequences on the first and second primers may be different from each other, in which case it requires the addition of two different non-thermostable DNA-dependent RNA polymerases capable of recognizing the respective promoter sequences. For the most effective amplification, the same promoter sequence may be used in the first and second promoters. Preferred is the use of T7 RNA polymerase and the corresponding promoter sequence. When a nucleic acid is amplified from DNA in a sample, the first primer having a promoter sequence for DNA-dependent RNA polymerase may be used under the same principle.

In order to detect single-stranded RNA to be amplified in the methods of the present invention, a detection probe having a sequence complementary to a target nucleic acid sequence may be used for the detection. For example, a capture probe is immobilized on a solid carrier, to which a nucleic acid amplified from a target nucleic acid in a sample is hybridized, and a detection probe having a label is hybridized to the amplified nucleic acid. The label of the hybridized detection probe is then measured to detect the target nucleic acid in the sample. Alternatively, several microliters of the reaction solution containing the amplified nucleic acid is added dropwise to a nylon membrane, and a detection probe, which is a radioactive or enzyme-labelled probe, is hybridized to the amplified nucleic acid. The radiation quantity or enzyme activity of the hybridized detection probe is then measured to detect the target nucleic acid in a sample.

The reagent kit for use in the amplification of a specific nucleic acid sequence according to the present invention comprises the above-described first and second primers, thermostable RNase H, non-thermostable DNA-dependent RNA polymerase, non-thermostable RNA-dependent DNA polymerase, non-thermostable DNA-polymerase, ribonucleoside triphosphates, deoxyribonucleoside triphosphates and a buffer.

The preferred thermostable RNase H is derived from *Thermus thermophilus*. The concentration thereof may be within the range of 0.001 to 0.1 U for 20 μl of the reaction system.

Examples of the non-thermostable DNA-dependent DNA polymerases include DNA polymerases derived from eucaryotic cells, including polymerase α or β; DNA polymerases isolated from mammalian tissues such as calf thymi; Klenow fragments of *E. coli* polymerase I; and bacteriophage T7 DNA polymerase. RNA-dependent DNA polymerases (reverse transcriptases) may also be used. Examples thereof include avian myoblastoma virus polymerase (AMV reverse transcriptase) and Maloney mouse leukemia virus polymerase (MMLV reverse transcriptase). Furthermore, other RNA-dependent DNA polymerases derived from eucaryotic cells may also be used. The concentration thereof is not particularly limited.

Examples of the non-thermostable DNA-dependent RNA polymerase include bacteriophage T7 RNA polymerase, T3 RNA polymerase, SP6 RNA polymerase, phage φII polymerase, Salmonella phage sp6 polymerase and Pseudomonas phage gh-1 polymerase. Particularly preferred are T7 RNA polymerase, T3 RNA polymerase and SP6 RNA polymerase. The concentration thereof is not particularly limited.

For each enzyme, a suitable buffer may be selected.

The amplification methods based on RNA replication according to the present invention can attain excellent advantageous effects by the use of thermostable RNase H that the number of amplification cycles is well increased at temperatures ranging from about 37° C. to about 45° C., as compared with the conventional methods in which non-thermostable RNase H is used, and the sensitivity of detection can be improved over these conventional methods.

The methods described above will be further illustrated by the following examples, which are not to be construed to limit the scope of the present invention in any way.

EXAMPLE 1

Synthesis of Oligonucleotides

Using DNA synthesizer model 391 (ABI), two oligonucleotides having the sequences shown in the Sequence Listing, i.e., the first primer having a promoter sequence for T7 RNA polymerase and a sequence complementary to cytomegalovirus mRNA (SEQ ID NO: 5) and the second primer having a sequence homologous to cytomegalovirus mRNA (SEQ ID NO: 4), were synthesized by the phosphoamidite method. The synthesis was carried out on a 0.2 M scale by the procedures following the ABI's manual. The deprotection of each oligonucleotide was achieved with ammonia water at 55° C. overnight. The purification was carried out by FPLC (Pharmacia) on a reverse phase column.

Preparation of RNA from Cytomegalovirus (CMV) Culture

Based on the procedures of Boom et al. (J. Clin. Microbiol., 28:495–503, 1990), RNA was prepared from CMV (strain AD 169) infected cells. More particularly, cell culture was treated in a lysis buffer containing Triton X-100 and guanidium thiocyanate (GuSCN), to which silica was added to absorb mRNA. The mRNA-carrying silica was washed two or three times with a washing buffer containing GuSCN, then washed with acetone to remove GuSCN, and dried. The elution was carried out with distilled water containing no nuclease. The eluate was subjected to serial dilution with the same distilled water.

Preparation of Detection Probe (1) Synthesis of Oligonucleotide having Linker Arm for CMV Detection Using the DNA synthesizer model 391 (ABI), one oligonucleotide having the sequence shown in the Sequence Listing, i.e., the detection probe (SEQ ID NO: 6), was synthesized by the phosphoamidite method. At this time, uridine having a linker arm at position 5, chemically synthesized from deoxyuridine, was incorporated into the above oligonucleotide by the synthesis method disclosed in JP-A 60-500717. This uridine can be substituted for any thymine (T) in the oligonucleotide; in this example, it was attached to the 5'-end. The deprotection of the synthesized linker-oligonucleotide was achieved with ammonia water at 55° C. over night. The purification was carried out by FPLC (Pharmacia) on a reverse column.

(2) Labelling of Linker-Oligonucleotide with Alkaline Phosphatase

Through the linker of the above linker-oligonucleotide, alkaline phosphatase was bound to the linker-oligonucleotide according to literature procedures (Nucleic Acids Research, vol. 14, p. 6114, 1986). The linker-oligonucleotide 1.5 $A_{260}$ was dissolved in 12.5 μl of 10 mM succinimidyl suberate (DSS) was added, and the reaction was allowed to proceed at room temperature for 2 minutes. The reaction mixture was subjected to gel filtration through a Sephadex G-25 column equilibrated with 1 mM $CH_3COONa$ (pH 5.0) to remove excess DSS.

The linker-oligonucleotide having the terminal amino group activated was further reacted with the 2-fold molar ratio of alkaline phosphatase (dissolved in 100 mM $NaHCO_3$ and 3 M HCl) at room temperature for 16 hours to yield an alkaline phosphatase-labelled probe. The resulting labelled probe was purified by FPLC (Pharmacia) on an anion exchange column, and fractions containing the labelled probe were collected and concentrated by ultrafiltration using Centricon 30K (Amicon).

Amplification

The reactions of amplification were effected according to literature procedures (J. Virol. Methods 35:273–286, 1991). In a 25 μl reaction system, the final concentration after addition of enzymes were adjusted to 40 mM Tris (pH 8.5); 20 mM $MgCl_2$; 40 mM KCl; 5 mM DTT; 15% DMSO; 1 mM dNTP; 4.1 mM rNTP; 0.2 μM the second primer (SEQ ID NO: 4); and 0.2 μM the first primer (SEQ ID NO: 5). The reaction system was mixed with the extracted RNA and heated at 65° C. for 5 minutes. This was followed by addition of 2.5 μg BSA, 12 U RNA Guard (Pharmacia), 20 U T7 RNA polymerase, 4 U AMV reverse transcriptase and 0.03 U thermostable RNase H derived from *Thermus thermophilus* to become 25 μl in total and then incubation at 41° C. for 3 hours.

Detection

After 1 μl of the reaction solution was added dropwise to a nylon membrane, the nucleic acid was immobilized thereon under alkaline conditions. This membrane was neutralized and then fixed under alkaline conditions. This membrane was neutralized and then placed in a hybridization bag, to which a hybridization buffer (5×SSC, 0.5% BSA, 0.5% PVP, 1% SDS) containing the above alkaline phosphatase-labelled nucleic acid probe was added, and hybridization was carried out at 50° C. for 15 minutes. The nylon membrane was taken out from the polymer bag, and osmotically washed with solution 1 (1×SSC, 1% SDS) at 50° C. for 10 minutes and then with solution 2 (1×SSC) at room temperature for 10 minutes. The membrane was placed in another hybridization bag, to which a substrate solution (0.1 M Tris, 0.1 M NaCl, 0.1 M $MgCl_2$, 0.3 M nitroblue tetrazolium, 0.3 mg/ml bromochlorophenol phosphate, pH 7.5) was added, and the bag was sealed and incubated at 37° C. for 30 minutes.

Results

Figure 5:
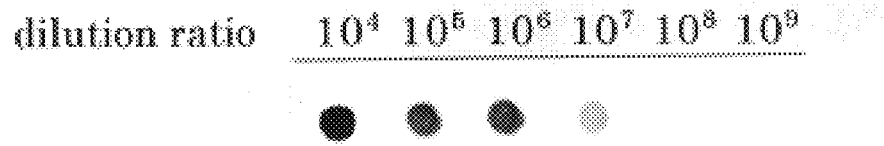
FIG. 5 is a hybridization pattern showing the results of hybridization in Example 1.

As shown in FIG. 5, the extracted RNA was detected up to the dilution ratio of $10^7$.

Comparative Example 1

Amplification

The reactions of amplification were effected according to literature procedures (J. Virol. Methods 35:273–286, 1991). In a 5 μl reaction system, the final concentration after addition of enzymes were adjusted to 40 mM Tris (pH 8.5); 20 mM $MgCl_2$; 40 mM KCl; 5 mM DTT; 15% DMSO; 1 mM dNTP; 4.1 mM rNTP; 0.2 μM the second primer (SEQ ID NO: 4); and 0.2 μM the first primer (SEQ ID NO: 5). The reaction system was mixed with the extracted RNA and heated at 65° C. for 5 minutes. This was followed by addition of 2.5 μg BSA, 12 U RNA Guard (Pharmacia), 20 U T7 RNA polymerase, 4 U AMV reverse transcriptase and 0.2 U RNase H derived from *E. coli* to become 25 μl in total and then incubation at 41° C. for 3 hours.

Detection

The detection was carried out in the same manner as described in Example 1.

Results

Figure 6:
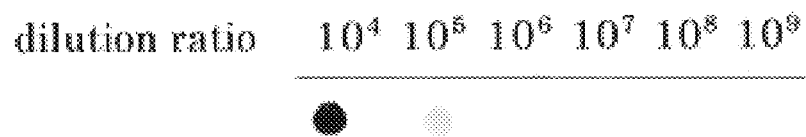
FIG. 6 is a hybridization pattern showing the results of hybridization in Comparative Example 1.

As shown in FIG. 6, the extracted RNA was detected up to the dilution ratio of $10^6$. The amplification was carried out in the same manner as described in Example 1. The sensitivity of detection was improved by the use of thermostable RNase H rather than the conventional *E. coli* RNase H (Pharmacia) as disclosed in the literature (J. Virol. Methods 35:273–286, 1991).

EXAMPLE 2

Synthesis of Oligonucleotides

The synthesis was carried out in the same manner as described in Example 1.

Preparation of DNA from CMV Culture

Cultured cells were suspended in 300 μl of 0.1 M $NaH_2PO_4$ (pH 7.0) buffer, to which 0.6 mg of proteinase K and 600 μl of lysis solution (8M urea, 0.25% SDS, 0.25% sodium laurylsarcosine, 50 mM EDTA, pH 7.6) were added, and the mixture was stirred to effect a reaction at 60° C. overnight.

The resulting lysate was extracted twice with phenol and once with chloroform, followed by ethanol precipitation. After another lysis, the lysate was treated with RNase for the complete cleavage of RNA, and extracted with twice with phenol and once with chloroform, followed by ethanol precipitation. The second lysis was carried out with distilled water containing neither RNase nor DNase, and the lysate was subjected to serial dilution with the same distilled water.

Preparation of Detection Probe

The preparation was carried out in the same manner as described above.

Amplification

The reactions of amplification were effected according to literature procedures (J. Virol. Methods 35:273–286, 1991).

In a 25 μl reaction system, the final concentration after addition of enzymes were adjusted to 40 mM Tris (pH 8.5); 20 mM MgCl$_2$; 40 mM KCl; 5 mM DTT; 15% DMSO; 1 mM dNTP; 4.1 mM rNTP; 0.2 μM the second primer (SEQ ID NO: 4); and 0.2 μM the first primer (SEQ ID NO: 5). The reaction system was mixed with the extracted DNA and heated at 95° C. for 5 minutes. The mixture was treated with 4 U AMV reverse transcriptase at 41° C. for 10 minutes. Further heating at 95° C. for 5 minutes was followed by addition of 2.5 μg BSA, 12 U RNA Guard (Pharmacia), 20 U T7 RNA polymerase, 4 U AMV reverse transcriptase and 0.03 U thermostable RNase H derived from *Thermus thermophilus* to become 25 μl and then incubation at 41° C. for 3 hours.

Detection

The detection was carried out in the same manner as described in Example 1.

Results

Figure 7:
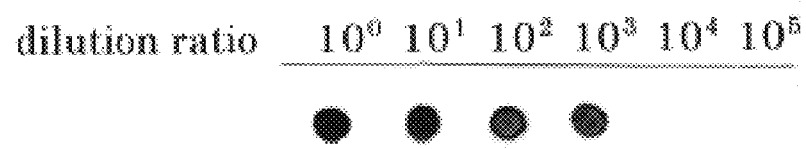
FIG. 7 is a hybridization pattern showing the results of hybridization in Example 2.

As shown in FIG. 7, the extracted DNA was detected up to the dilution ratio of $10^4$.

Comparative Example 2

Amplification

The reactions of amplification were effected according to literature procedures (J. Virol. Methods 35:273–286, 1991). In a 5 μl reaction system, the final concentration after addition of enzymes were adjusted to 40 mM Tris (pH 8.5); 20 mM MgCl$_2$; 40 mM KCl; 5 mM DTT; 15% DMSO; 1 mM dNTP; 4.1 mM rNTP; 0.2 μM the second primer (SEQ ID NO: 4); and 0.2 μM the first primer (SEQ ID NO: 5). The reaction system was mixed with the extracted DNA and heated at 95° C. for 5 minutes. The mixture was treated with 4 U AMU reverse transcriptase at 41° C. for 10 minutes. Further heating at 95° C. for 5 minutes was followed by addition of 2.5 μg BSA, 12 U RNA Guard (Pharnacia), 20 U T7 RNA polymerase, 4 U AMU reverse transcriptase and 0.2 U *E. coli* RNase H to become 25 μl and then incubation at 41° C. for 3 hours.

Detection

The detection was carried out in the same manner as described in Example 1.

Results

Figure 8:
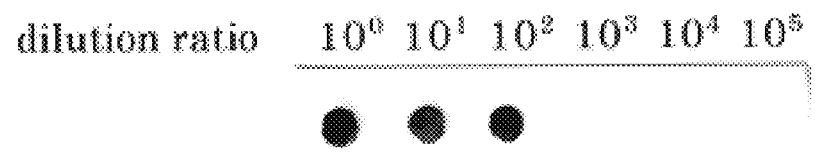
FIG. 8 is a hybridization pattern showing the results of hybridization in Comparative Example 2.

As shown in FIG. 8, the extracted DNA was detected up to the dilution ratio of $10^3$. The amplification was carried out in the same manner as described in Example 2, except that thermostable RNase H was used instead of *E. coli* RNase H. The sensitivity of detection was improved by the use of thermostable RNase H rather than the conventional *E. coli* RNase H.

EXAMPLE 3

Synthesis of Oligonucleotides

Using DNA synthesizer model 391 (ABI), two oligonucleotides having the sequences shown in the Sequence Listing, i.e., the first primer having a promoter sequence for T7 RNA polymerase and a sequence complementary to cytomegalovirus mRNA (SEQ ID NO: 5) and the second primer having a promoter sequence for T7 RNA polymerase and a sequence homologous to cytomegalovirus mRNA (SEQ ID NO: 7), were synthesized by the phosphoamidite method. The synthesis was carried out on a 0.2 M scale by the procedures following the ANBI's manual. The deprotection of each oligonucleotide was achieved with ammonia water at 55° C. overnight. The purification was carried out by FPLC (Pharmacia) on a reverse column.

Amplification

The reactions of amplification were effected in the same manner as described in Example 1.

Detection

The detection was carried out in the same manner as described in Example 1.

Results

Figure 9:
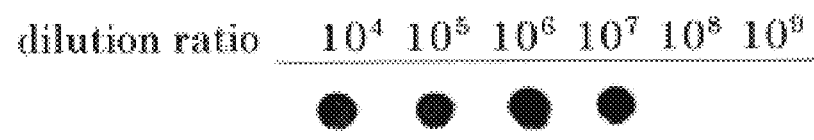
FIG. 9 is a hybridization pattern showing the results of hybridization in Example 3.

As shown in FIG. 9, the extracted RNA was detected up to the dilution ratio of $10^7$. The sensitivity of detection was equal to that obtained in Example 1; however, the spot for $10^7$-fold dilution in Example 3 was thicker than that obtained in Example 1. It is, therefore, believed that the amount of the detected nucleic acid is increased because both single-stranded RNA and its complementary sequence are amplified.

What is claimed is:

1. A method for nucleic acid amplification at a temperature between 37° and 45° C., wherein single-stranded RNA (−) is prepared from RNA (+) as a target nucleic acid and the copy number of the single-stranded RNA (−) is increased, comprising the steps of:

(1) optionally extracting RNA (+) as a target nucleic acid from a sample;

(2) hybridizing a first primer to the RNA (+) in step (1) as a template, the first primer having a sequence complementary to the RNA (+) sequence and a promoter sequence for non-thermostable DNA-dependent RNA polymerase on the 5'-end thereof; and effecting a reaction of DNA extension with non-thermostable RNA-dependent DNA polymerase to yield an RNA/DNA hybrid extension product;

(3) cleaving the RNA from the RNA/DNA hybrid extension product in step (2) with thermostable ribonuclease H that specifically cleaves only RNA from any RNA/DNA hybrid, to yield single-stranded DNA;

(4) hybridizing a second primer to the single-stranded DNA in step (3) as a template, the second primer having a sequence complementary to the single-stranded DNA sequence; and effecting a reaction of DNA extension with non-thermostable DNA-dependent DNA polymerase to yield a double-stranded DNA intermediate having a functionable promoter sequence upstream from the 5'-end thereof, wherein the nucleic acid sequence of the first primer is complementary to the target nucleic acid, RNA (+) sequence, and the nucleic acid sequence of the second primer is homologous to the target nucleic acid, RNA (+) sequence, and the 3'-end of the first primer is directed to the 3'-end of the second primer on the complementary strand;

(5) increasing the copy number of single-stranded RNA (−) from the double-stranded DNA intermediate in step (4) with non-thermostable DNA-dependent RNA polymerase that recognizes the promoter sequence therefor;

(6) hybridizing the second primer to the single-stranded RNA (−) in step (5) as a template, the second primer having a sequence complementary to the single stranded RNA (−) sequence, which second primer is the same as that used in step (4) and having a sequence homologous to the RNA (+) sequence; and effecting a reaction of DNA extension with non-thermostable RNA-dependent DNA polymerase to yield an RNA/DNA hybrid extension product;

(7) cleaving the RNA from the RNA/DNA hybrid extension product in step (6) with thermostable ribonuclease H that specifically cleaves only RNA from any RNA/DNA hybrid, to yield single-stranded DNA;

(8) hybridizing the first primer to the single-stranded DNA in step (7) as a template, the first primer having a sequence complementary to the single-stranded DNA sequence and a promoter sequence for non-thermostable DNA-dependent RNA polymerase on the 5'-end thereof, which first primer is the same as that used in step (2) and having a sequence complementary to the RNA (+) sequence; and effecting a reaction of DNA extension with non-thermostable DNA-dependent DNA polymerase to yield a double-stranded DNA intermediate having a functionable promoter sequence upstream from the 5'-end thereof;

(9) increasing the copy number of single-stranded RNA (−) from the double-stranded DNA intermediate in step (8) with non-thermostable DNA-dependent RNA polymerase that recognizes the promoter sequence therefor; and

(10) optionally repeating steps (6) to (9) with the resulting single-stranded RNA (−) as a template.

2. A method for nucleic acid amplification at a temperature between 37° and 45°0 C., wherein single-stranded RNAs (+) and (−) are prepared from RNA (+) as a target nucleic acid and the copy numbers of the single-stranded RNAs (+) and (−) are increased, comprising the steps of:

(1) optionally extracting RNA (+) as a target nucleic acid from a sample;

(2) hybridizing a first primer to the RNA (+) in step (1) as a template, the first primer having a sequence complementary to the RNA (+) sequence and a promoter sequence for non-thermostable DNA-dependent RNA polymerase on the 5'-end thereof; and effecting a reaction of DNA extension with non-thermostable RNA-dependent DNA polymerase to yield an RNA/DNA hybrid extension product;

(3) cleaving the RNA from the RNA/DNA hybrid extension product in step (2) with thermostable ribonuclease H that specifically cleaves only RNA from any RNA/DNA hybrid, to yield single-stranded DNA;

(4) hybridizing a second primer to the single-stranded DNA in step (3) as a template, the second primer having a sequence complementary to the single-stranded DNA sequence and a promoter sequence for non-thermostable DNA-dependent RNA polymerase on the 5'-end thereof, and effecting a reaction of DNA extension with non-thermostable DNA-dependent DNA polymerase to yield a double-stranded DNA intermediate having functionable promoter sequences upstream from the 5'-end thereof; wherein the nucleic acid sequence of the first primer is complementary to the target nucleic acid, RNA (+) sequence, the nucleic acid sequence of the second primer is homologous to the target nucleic acid, RNA (+) sequence, and the 3'-end of the first primer is directed to the 3'-end of the second primer on the complementary strand;

(5) increasing the copy numbers of single-stranded RNAs (+) and (−) from the double-stranded DNA intermediate in step (4) with non-thermostable DNA-dependent RNA polymerase that recognizes the promoter sequence therefor;

(6) hybridizing the first and second primers, which are the same as used in steps (2) and (4), respectively, to the single-stranded RNAs (+) and (−) in step (5), respectively, as templates; and effecting reactions of DNA extension with non-thermostable RNA-dependent DNA polymerase to yield RNA/DNA hybrid extension products;

(7) cleaving the RNA from the RNA/DNA hybrid extension products in step (6) with thermostable ribonuclease H that specifically cleaves only RNA from any RNA/DNA hybrid, to yield single-stranded DNAs (+) and (−);

(8) hybridizing the first and second primers, which are the same as used in steps (2) and (4), respectively, to the single-stranded DNAs (+) and (−) in step (7), respectively, as a template; and effecting reactions of DNA extension with non-thermostable DNA-dependent DNA polymerase to yield a double-stranded DNA intermediate having functionable promoter sequences upstream from the 5'-end thereof;

(9) increasing the copy numbers of single-stranded RNAs (+) and (−) from the double-stranded DNA intermediate in step (8) with non-thermostable DNA-dependent RNA polymerase that recognizes the promoter sequence therefor; and

(10) optionally repeating steps (6) to (9) with the resulting single-stranded RNAs (+) and (−) as templates.

3. A method for nucleic acid amplification at a temperature between 37° and 45° C., wherein single-stranded RNA (−) is prepared from DNA (+) as a target nucleic acid sequence and the copy number of the single-stranded RNA (−) is increased, comprising the steps of:

(1) optionally extracting DNA (+) as a target nucleic acid sequence from a sample;

(2) hybridizing a first primer to the DNA (+) in step (1), the first primer having a sequence complementary to the DNA (+) sequence and a promoter sequence for non-thermostable DNA-dependent DNA polymerase on the 5'-end thereof, and effecting a reaction of DNA extension with non-thermostable DNA-dependent DNA polymerase to yield a double stranded DNA;

(3) separating single-stranded DNA from the double-stranded DNA in step (2) by denaturation;

(4) hybridizing a second primer to the single-stranded DNA in step (3), the second primer having a sequence homologous to the DNA (+) sequence; and effecting a reaction of DNA extension with non-thermostable DNA-dependent DNA polymerase to yield a double-stranded DNA intermediate having a functionable promoter sequence upstream from the 5'-end thereof;

(5) synthesizing a plurality of single-stranded RNAs (−) from the double stranded DNA intermediate in step (4) with non-thermostable DNA-dependent RNA polymerase;

(6) hybridizing a second primer to the single-stranded RNA (−) in step (5) as a template, the second primer having a sequence complementary to the single-stranded RNA (−) sequence, which second primer is the same as that used in step (4) and having a sequence homologous to the DNA (+) sequence; and effecting a reaction of DNA extension with non-thermostable RNA-dependent DNA polymerase to yield an RNA/DNA hybrid extension product;

(7) cleaving the RNA from the RNA/DNA hybrid extension product in step (6) with thermostable ribonuclease H that specifically cleaves only RNA from any RNA/DNA hybrid, to yield single-stranded DNA;

(8) hybridizing a first primer to the single-stranded DNA in step (7) as a template, the first primer having a sequence complementary to the single-stranded DNA sequence and a promoter sequence for non-thermostable DNA-dependent DNA polymerase on the 5'-end thereof, which first primer is the same as that used in step (2) and having a sequence complementary to the DNA (+) sequence; and effecting a reaction of DNA extension with non-thermostable DNA-dependent DNA polymerase to yield a double-stranded DNA intermediate having a functionable promoter sequence upstream from the 5'-end thereof;

(9) increasing the copy number of single-stranded RNA (−) from the double-stranded DNA intermediate in step (8) with non-thermostable DNA-dependent RNA polymerase that recognizes the promoter sequence therefor; and

(10) optionally repeating steps (6) to (9) with the resulting single-stranded RNA (−) as a template.

4. A method for nucleic acid amplification at a temperature between 37° and 45° C., wherein single-stranded RNAs (+) and (−) are prepared from DNA (+) as a target nucleic acid and the copy number of the single-stranded RNAs (+) and (−) is increased, comprising the steps of:

(1) optionally extracting DNA (+) as a target nucleic acid from a sample;

(2) hybridizing a first primer to the DNA (+) in step (1), the first primer having a sequence complementary to the DNA (+) sequence and a promoter sequence for non-thermostable DNA-dependent RNA polymerase on the 5'-end thereof, and effecting a reaction of DNA extension with non-thermostable DNA-dependent DNA polymerase to yield a double-stranded DNA;

(3) separating single-stranded DNA from the double-stranded DNA in step (2) by denaturation;

(4) hybridizing a second primer to the single-stranded DNA in step (3), the second primer having a sequence homologous to the DNA (+) sequence and a promoter sequence for non-thermostable DNA-dependent DNA polymerase on the 5'-end thereof; and effecting a reaction of DNA extension with non-thermostable DNA-dependent DNA polymerase to yield a double-stranded DNA intermediate having functionable promoter sequences upstream from the 5'-end thereof;

(5) synthesizing a plurality of single-stranded RNAs (+) and (−) from the double-stranded DNA intermediate in step (4) with non-thermostable DNA-dependent RNA polymerase;

(6) hybridizing the first and second primers, which are the same as used in steps (2) and (4), respectively, to the single-stranded RNAs (+) and (−) in step (5), respectively, as templates; and effecting reactions of DNA extension with non-thermostable RNA-dependent DNA polymerase to yield RNA/DNA hybrid extension products;

(7) cleaving the RNA from the RNA/DNA hybrid extension products in step (6) with thermostable ribonuclease H that specifically cleaves only RNA from any RNA/DNA hybrid, to yield single-stranded DNAs (+) and (−);

(8) hybridizing the first and second primers, which are the same as used in steps (2) and (4), respectively, to the single-stranded DNAs (+) and (−) in step (7), respectively, as templates; and effecting reactions of DNA extension with non-thermostable DNA-dependent DNA polymerase to yield a double-stranded DNA intermediate having functionable promoter sequences upstream from the 5'-end thereof;

(9) increasing the copy numbers of single-stranded RNAs (+) and (−) from the double-stranded DNA intermediate in step (8) with non-thermostable DNA-dependent RNA polymerase that recognizes the promoter sequence therefor; and

(10) optionally repeating steps (6) to (9) with the resulting single-stranded RNAs (+) and (−) as templates.

5. The method for nucleic acid amplification according to claim 3, wherein the denaturation is achieved by heat, acid or alkali treatment.

6. The method for nucleic acid amplification according to claim 1, wherein the thermostable ribonuclease H is derived from *Thermus thermophilus*.

7. The method for nucleic acid amplification according to claim 1, wherein the non-thermostable DNA-dependent DNA polymerase is reverse transcriptase.

8. The method for nucleic acid amplification according to claim 1, wherein the non-thermostable RNA-dependent DNA polymerase is reverse transcriptase.

9. The method for nucleic acid amplification according to claim 7, wherein the reverse transcriptase is derived from avian myeloblastosis virus.

10. The method for nucleic acid amplification according to claim 8, wherein the reverse transcriptase is derived from avian myeloblastosis virus.

11. The method for nucleic acid amplification according to claim 1, wherein the non-thermostable DNA-dependent RNA polymerase is T7 RNA polymerase, T3 RNA polymerase or SP6 RNA polymerase.

12. The method for nucleic acid amplification according to claim 1, wherein the promoter sequence for non-thermostable DNA-dependent RNA polymerase is a promoter sequence for T7 RNA polymerase, for T3 RNA polymerase or for SP6 RNA polymerase.

13. A method for the detection of a target nucleic acid in a sample, comprising amplifying a target nucleic acid in a sample by the method for nucleic acid amplification according to claim 1; hybridizing the amplified nucleic acid to a detection probe; and detecting the hybridized nucleic acid.

14. A reagent kit for use in the amplification of a specific nucleic acid, comprising the reagents:

(a) a first primer having a sequence complementary to the sequence of RNA(+) as the nucleic acid and a promoter sequence for non-thermostable DNA-dependent RNA polymerase on the 5'-end thereof;

(b) a second primer having a sequence homologous to the RNA (+) sequence;

(c) thermostable ribonuclease H;

(d) non-thermostable DNA-dependent RNA polymerase;

(e) non-thermostable RNA-dependent DNA polymerase;

(f) non-thermostable DNA-dependent DNA polymerase;

(g) ribonucleoside triphosphates;

(h) deoxyribonucleoside triphosphates; and (i) a buffer.

15. The reagent kit for use in the amplification of a specific nucleic acid according to claim 14, wherein said second primer further has a promoter sequence for non-thermostable DNA-dependent RNA polymerase on the 5'-end thereof.

16. The reagent kit for use in the amplification of a specific nucleic acid according to claim 14, wherein the thermostable ribonuclease H is derived from *Thermus thermophilus*.

17. The reagent kit for use in the amplification of a specific nucleic acid according to claim 14, wherein the non-thermostable DNA-dependent DNA polymerase is reverse transcriptase.

18. The reagent kit for use in the amplification of a specific nucleic acid according to claim 14, wherein the non-thermostable RNA-dependent DNA polymerase is reverse transcriptase.

19. The reagent kit for use in the amplification of a specific nucleic acid according to claim 17, wherein the reverse transcriptase is derived from avian myeloblastosis virus.

20. The reagent kit for amplification of a specific nucleic acid according to claim 18, wherein the reverse transcriptase is derived from avian myeloblastosis virus.

21. The reagent kit for use in the amplification of a specific nucleic acid according to claim 14, wherein the non-thermostable DNA-dependent RNA polymerase is T7 RNA polymerase, T3 RNA polymerase or SP6 RNA polymerase.

22. The reagent kit for use in the amplification of a specific nucleic acid according to claim 14, wherein the promoter sequence for non-thermostable DNA-dependent RNA polymerase is a promoter sequence for T7 RNA polymerase, for T3 RNA polymerase or for SP6 RNA polymerase.

23. The method for nucleic acid amplification according to claim 2, wherein the thermostable ribonuclease H is derived from *Thermus thermophilus*.

24. The method for nucleic acid amplification according to claim 2, wherein the non-thermostable DNA-dependent DNA polymerase is reverse transcriptase.

25. The method for nucleic acid amplification according to claim 2, wherein the non-thermostable RNA-dependent DNA polymerase is reverse transcriptase.

26. The method for nucleic acid amplification according to claim 24, wherein the reverse transcriptase is derived from avian myeloblastosis virus.

27. The method for nucleic acid amplification according to claim 25, wherein the reverse transcriptase is derived from avian myeloblastosis virus.

28. The method for nucleic acid amplification according to claim 2, wherein the non-thermostable DNA-dependent RNA polymerase is T7 RNA polymerase, T3 RNA polymerase or SP6 RNA polymerase.

29. The method for nucleic acid amplification according to claim 2, wherein the promoter sequence for non-thermostable DNA-dependent RNA polymerase is a promoter sequence for T7 RNA polymerase, for T3 RNA polymerase or for SP6 RNA polymerase.

30. A method for the detection of a target nucleic acid in a sample, comprising amplifying a target nucleic acid in a sample by the method for nucleic acid amplification according to claim 2; hybridizing the amplified nucleic acid to a detection probe; and detecting the hybridized nucleic acid.

31. The method for nucleic acid amplification according to claim 3, wherein the thermostable ribonuclease H is derived from *Thermus thermophilus*.

32. The method for nucleic acid amplification according to claim 3, wherein the non-thermostable DNA-dependent DNA polymerase is reverse transcriptase.

33. The method for nucleic acid amplification according to claim 3, wherein the non-thermostable RNA-dependent DNA polymerase is reverse transcriptase.

34. The method for nucleic acid amplification according to claim 32, wherein the reverse transcriptase is derived from avian myeloblastosis virus.

35. The method for nucleic acid amplification according to claim 33, wherein the reverse transcriptase is derived from avian myeloblastosis virus.

36. The method for nucleic acid amplification according to claim 3, wherein the non-thermostable DNA-dependent RNA polymerase is T7 RNA polymerase, T3 RNA polymerase or SP6 RNA polymerase.

37. The method for nucleic acid amplification according to claim 3, wherein the promoter sequence for non-thermostable DNA-dependent RNA polymerase is a promoter sequence for T7 RNA polymerase, for T3 RNA polymerase or for SP6 RNA polymerase.

38. A method for the detection of a target nucleic acid in a sample, comprising amplifying a target nucleic acid in a sample by the method for nucleic acid amplification to form a hybridized nucleic acid according to claim 3; hybridizing the amplified nucleic acid to a detection probe; and detecting the hybridized nucleic acid.

39. The method for nucleic acid amplification according to claim 4, wherein the thermostable ribonuclease H is derived from *Thermus thermophilus*.

40. The method for nucleic acid amplification according to claim 4, wherein the non-thermostable DNA-dependent DNA polymerase is reverse transcriptase.

41. The method for nucleic acid amplification according to claim 4, wherein the non-thermostable RNA-dependent DNA polymerase is reverse transcriptase.

42. The method for nucleic acid amplification according to claim 40, wherein the reverse transcriptase is derived from avian myeloblastosis virus.

43. The method for nucleic acid amplification according to claim 41, wherein the reverse transcriptase is derived from avian myeloblastosis virus.

44. The method for nucleic acid amplification according to claim 4, wherein the non-thermostable DNA-dependent RNA polymerase is T7 RNA polymerase, T3 RNA polymerase or SP6 RNA polymerase.

45. The method for nucleic acid amplification according to claim 4, wherein the promoter sequence for non-thermostable DNA-dependent RNA polymerase is a promoter sequence for T7 RNA polymerase, for T3 RNA polymerase or for SP6 RNA polymerase.

46. A method for the detection of a target nucleic acid in a sample, comprising amplifying a target nucleic acid in a sample by the method for nucleic acid amplification to form a hybridized nucleic acid according to claim 4; hybridizing the amplified nucleic acid to a detection probe; and detecting the hybridized nucleic acid.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid (synthesized DNA)

(iii) FEATURE:
      (A) NAME/KEY: promoter (B) LOCATION: 1..25
        (C) IDENTIFICATION METHOD: by similarity with known
            sequence or to an
            established consensus
        (D) OTHER INFORMATION: promoter sequence
            for T7 RNA polymerase (xi) SEQUENCE DESCRIPTION: SEQ ID NO:1:

AATTCTAATA CGACTCACTA TAGGG                                              25

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (synthesized DNA)

(iii) FEATURE:
        (A) NAME/KEY: promoter
        (B) LOCATION: 1..17
        (C) IDENTIFICATION METHOD: by similarity with known
            sequence or to an
            established consensus
        (D) OTHER INFORMATION: promoter sequence
            for T3 RNA polymerase (xi) SEQUENCE DESCRIPTION: SEQ ID NO:2:

ATTAACCCTC ACTAAAG                                                       17

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (synthesized DNA)

(iii) FEATURE:
        (A) NAME/KEY: promoter
        (B) LOCATION: 1..17
        (C) IDENTIFICATION METHOD: by similarity with known
            sequence or to an
            established consensus
        (D) OTHER INFORMATION: promoter sequence
            for SP6 RNA polymerase (xi) SEQUENCE DESCRIPTION: SEQ ID NO:3:

ATTTAGGTG ACACTATA                                                       17

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (synthesized DNA)

(iii) FEATURE:
        (B) LOCATION: 1..20
        (C) IDENTIFICATION METHOD: by similarity with known
            sequence or to an
            established consensus
        (D) OTHER INFORMATION: having a sequence homologous to
            mRNA of cytomegalovirus (xi) SEQUENCE DESCRIPTION: SEQ ID NO:4:

```
ACTGTCTGCA GGACGCCGTA                                                           20
```

(2) INFORMATION FOR SEQ ID NO:5:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid (synthesized DNA)

(iii) FEATURE:
        (A) NAME/KEY: promoter
        (B) LOCATION: 1..27
        (C) IDENTIFICATION METHOD: by similarity with known
            sequence or to an
            established consensus
        (D) OTHER INFORMATION: promoter sequence
            for T7 RNA polymerase (iii) FEATURE:
        (B) LOCATION: 28..47
        (C) IDENTIFICATION METHOD: by similarity with known
            sequence or to
            an established consensus
        (D) OTHER INFORMATION: having a sequence complementary
            to mRNA of cytomegalovirus (xi) SEQUENCE DESCRIPTION: SEQ ID NO:5:

```
AATTCTAATA CGACTCACTA TAGGGAGGAG GTGTAGATAC GGATCTG                             47
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (synthesized DNA)

(iii) FEATURE:
        (B) LOCATION: 1..27
        (C) IDENTIFICATION METHOD: by similarity with known
            sequence or to an
            established consensus
        (D) OTHER INFORMATION: having a sequence homologous to
            mRNA of cytomegalovirus (xi) SEQUENCE DESCRIPTION: SEQ ID NO:6:

```
ATTCCGTTGC GGCGTGTCAT CTTT                                                      24
```

(2) INFORMATION FOR SEQ ID NO:7:

(i) SEQUENCE CHARACTERISTICS:
        (A) LENGTH: 47 base pais
        (B) TYPE: nucleic acid
        (C) STRANDEDNESS: single strand
        (D) TOPOLOGY: linear (ii) MOLECULE TYPE: other nucleic acid (synthesized DNA)

(iii) FEATURE:
        (A) NAME/KEY: promoter
        (B) LOCATION: 1..27
        (C) IDENTIFICATION METHOD: by similarity with known
            sequence or to an
            established consensus
        (D) OTHER INFORMATION: promoter sequence
            for T7 RNA polymerase (iii) FEATURE:
        (B) LOCATION: 28..47
        (C) IDENTIFICATION METHOD: by similarity with known

```
                sequence or to an
                established consensus
        (D) OTHER INFORMATION: having a sequence homologous to
                mRNA of cytomegalovirus (xi) SEQUENCE DESCRIPTION: SEQ ID NO:7:

AATTCTAATA CGACTCACTA TAGGGAGACT GTCTGCAGGA CGCCGTA                          47
```